United States Patent [19]

Bowman et al.

[11] Patent Number: 4,950,270
[45] Date of Patent: Aug. 21, 1990

[54] CANNULATED SELF-TAPPING BONE SCREW

[75] Inventors: Jerald A. Bowman; Richard V. Zile, both of Warsaw, Ind.

[73] Assignee: Boehringer Mannheim Corporation, Indianapolis, Ind.

[21] Appl. No.: 306,474

[22] Filed: Feb. 3, 1989

[51] Int. Cl.⁵ .............................................. A61F 5/04
[52] U.S. Cl. .................................... 606/72; 606/73
[58] Field of Search ........ 128/92 YE, 92 YF, 92 YV, 128/92 R, 92 YK, 92 YT; 623/13, 39

[56] References Cited

U.S. PATENT DOCUMENTS

| | | | |
|---|---|---|---|
| 2,242,003 | 5/1941 | Lorenzo | 128/92 YV |
| 2,267,925 | 12/1941 | Johnston | 128/92 YT |
| 4,463,753 | 8/1984 | Gustilo | 128/92 YE |
| 4,537,185 | 8/1985 | Stednitz | 128/92 YE |
| 4,744,793 | 5/1988 | Parr et al. | 623/13 |

FOREIGN PATENT DOCUMENTS

| | | | |
|---|---|---|---|
| 0282789 | 9/1988 | European Pat. Off. | 128/92 R |
| 0094371 | 6/1969 | France | 128/92 YF |

OTHER PUBLICATIONS

John B. McGirrty, Techniques in Orthopaedics, vol. 5, Anthroscopic Surgery Update, 1985, pp. 73-77.

Primary Examiner—Mickey Yu
Assistant Examiner—Charles H. Sam
Attorney, Agent, or Firm—Barnes & Thornburg

[57] ABSTRACT

A fluted and cannulated self-tapping bone screw which can be guided into proper position using a guide pin that slidably fits in the cannula of the bone screw. The flutes have cutting edges centered on axial centerline of the cannula.

14 Claims, 1 Drawing Sheet

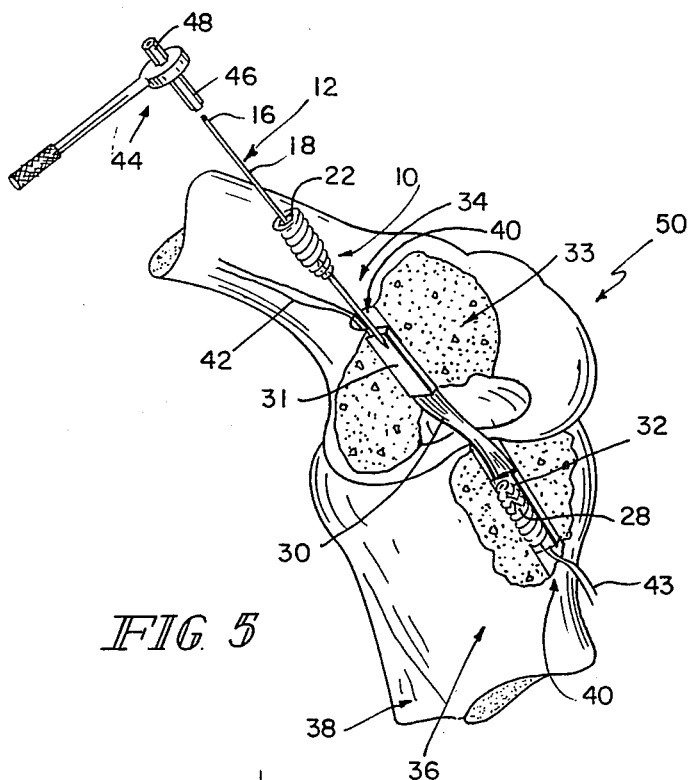
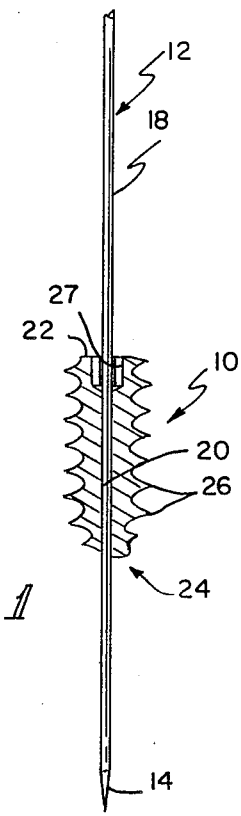
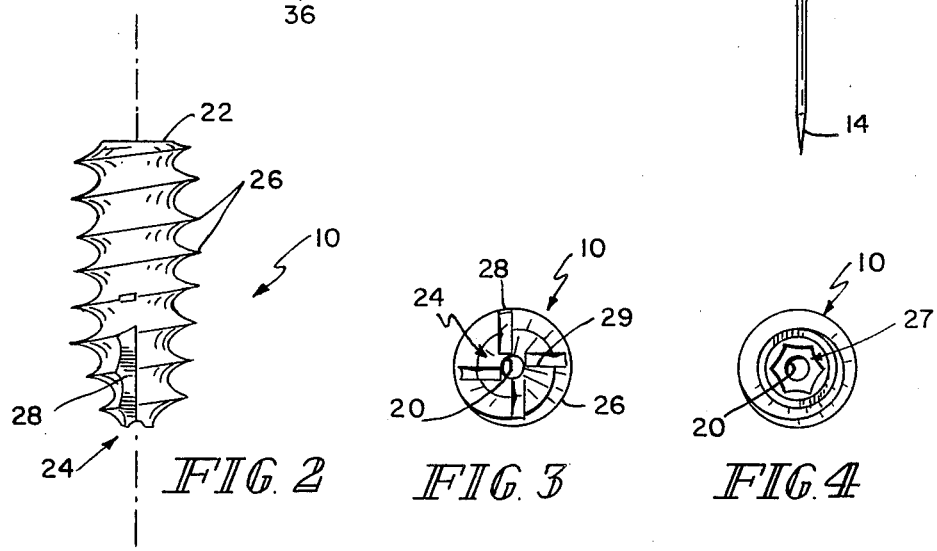

CANNULATED SELF-TAPPING BONE SCREW

BACKGROUND AND SUMMARY OF THE INVENTION

The present invention relates to a cannulated bone fixation screw that can be inserted with the aid of a guide pin. The cannulated screw according to the present invention is useful for the surgical repair of injured bones, tendons, and ligaments.

A relatively common injury involves complete or partial detachment of tendons, ligaments or other soft tissues from their bony attachment points. Partial detachment, commonly known as a sprain, will generally heal given sufficient time. However, if the ligament or tendon is completely detached from the bony attachment points, or is severed by a traumatic injury, partial or permanent disability can result if surgical attention is not given soon after the injury. Detachment of ligaments frequently occurs among certain types of athletes such as football players due to the unusual stresses placed on ligaments during normal play. Fortunately, detachment due to external trauma or mechanical overextension of a ligament or tendon can be surgically corrected in many cases.

A typical surgical correction of a tendon or ligament injury involves the fixed attachment of the tendon or ligament substitute to the area of normal bony attachment so that regrowth and reattachment of the tendon or ligament substitute to the bone is enabled. Attachment of the ligament substitute to the bone is ensured by the use of bone attachment means such as metal staples, sutures over buttons, or cancellous bone screws. The ligament substitute to bone attachment means must be rigidly situated so that regrowth of the ligament substitute in the bony area of the attachment point is uninterrupted by any later disattachment due to stress.

The prior art devices for reattachment are not uniformly successful, especially in those instances when the occupation or lifestyle of the recipient of the reattachment procedure is very active. A common problem with the prior art attachment methods is their failure under the normal tensile loads to which the attachment means is subjected, which can cause further soft tissue damage requiring more corrective surgery. A further problem with conventional cancellous bone screws is the difficulty encountered in the successful insertion of the screw in the correct position and orientation due to inadequate screw size, poor bone quality, or poor surgical technique. Accurate positioning of the screw is necessary to ensure a close interference fit where the screw imparts a significant compressive load against the bone plug so that the bone plug becomes intimate with the bone hole.

It is accordingly the object of the present invention to provide an attachment device for reconnection of detached or severed soft tissues to their bony attachment points that is capable of being accurately positioned.

It is further object of the present invention to provide a self-tapping bone screw using flutes cut into the threads of the bone screw, with the bone screw further having an axial cannula suitable for use in conjunction with a guide pin for proper positioning of the bone screw in a bone bore hole.

Another object of this invention is to provide a fluted, self-tapping bone screw having an axial cannula suitable for use in conjunction with a guide pin for proper positioning of the bone screw in a bone bore hole so that an interference fit between a bone plug with attached ligament substitute, the bore hole walls, and the bone screw is created.

One further object of this invention is to provide a method for the reattachment of soft tissues to bony attachment points by providing a fluted, self-tapping bone screw having an axial cannula suitable for use in conjunction with a guide pin that ensures proper positioning of the bone screw.

According to the present invention, an apparatus and method suitable for providing a secure attachment point in cancellous bone is provided. The apparatus includes a bone screw having an axially centered cannula with a diameter corresponding to the diameter of a guide pin that has been preinserted into a bone bore hole. The bone screw is self-tapping, having flutes cut into the threads that act to cut internal threads into cancellous bone in the bone bore. A common method of employment of the bone screw of the present invention is to provide an interference fit between a bone plug attached to a ligament substitute and inserted into the bone bore hole, and the sides of the bone bore hole. In this situation the bone screw will act to permanently compress the bone plug against the bore hole wall, providing a stable attachment point to permit the bone plug and the bone bore hole to become one to permit for ligament substitute regrowth and revitalization.

The objects and advantages of the present invention will become more apparent with reference to the following drawings. It should be understood that the drawings are for illustrative purposes only, and are not meant to limit or circumscribe the scope or intent of the claims made to the present invention.

BRIEF DESCRIPTION OF THE DRAWINGS

FIG. 1 is a cross-sectional side view of the bone screw with the guide pin situated in the axial cannula;

FIG. 2 is a side view of the bone screw illustrating the position of the fluting cut into the threads of the bone screw;

FIG. 3 is a plan view of the point of a bone screw, showing the positioning of the off-axis fluting cut into the threads of the bone screw and the axially centered cannula;

FIG. 4 is a plan view of the head of a bone screw, showing the hexagonal screw head and the positioning of the axially centered cannula; and FIG. 5 shows a portion of the human femur bone and human tibia bone with a cut-away section showing the bore hole used for screw emplacement.

DETAILED DESCRIPTION OF THE DRAWINGS

A cross-sectional side view of a bone screw 10 according to the present invention is shown in FIG. 1. The bone screw 10 is shown positioned over a guide pin 12. The guide pin 12 is preferably constructed of a hard steel or steel alloy and consists of three parts, a guide pin point 14, a guide pin head 16 and a guide pin shank 18. In a preferred embodiment the guide pin 12 is a cylindrical pin, with a sharpened guide pin point 14 at one end of the cylinder and a gently rounded guide pin head 16 at the end opposite the guide pin point 14. The diameter of the guide pin 12 is such that a sliding fit in the cannula 20 of bone screw 10 is enabled.

The bone screw 10, having a cannula 20 through which the guide pin 12 may be inserted, can also be divided into three major parts for description purposes. The bone screw 10 has a roughly cylindrical shape with a bone screw head 22 and a bone screw point 24 situated at opposite ends. Between the bone screw head 22 and the bone screw point 24 are bone screw threads 26. The bone screw threads 26 have a normal helical winding for screwing insertion into a material. In a preferred embodiment the diameter of the bone screw 10 may decrease from a maximal diameter near the bone screw head 22 to a minimum at the bone screw point 24. This tapering feature increases the ease of screwing insertion into a material.

The bone screw 10 is ideally constructed of a biocompatible material suitable for permanent or long term emplacement in association with cancellous bone and soft tissues. The material may also be coated with various substances that promote osteointegration, such as hydroxyapatite, various plasma spray coatings, or porous coated alloys obtained by coating cobalt-chromium-molybdenum with a porous layer of beads. Substrate materials suitable for the bone screw 10 include stainless steel and stainless steel alloys, titanium and titanium alloys, and certain biodegradable materials specially tailored for hardness, tensile and compressive strength and arbitrarily defined absorption rates.

The bone screw head 22 is fitted with an engaging means 27 to enable threading into a desired material by the bone screw 10. Diverse embodiments of an engaging means 27 are suitable for this purpose, including square or hexagonal cavities in the bone screw head 22, unitary or multiple narrow slots, or grooved cylindrical cavities. The only necessary limitation on the engaging means 27 is that clear passage to the cannula 20 by a guide pin 12 is not impaired. A plan view of bone screw head 22 with the engaging means 27 is shown in FIG. 4. Additionally, threads (not shown) could be formed in the cannula 20 to permit an extraction tool (not shown) to engage these threads to permit easy extraction of the screw 10.

The screwing insertion of bone screw 10 is facilitated by flutes 28 (one of which is shown in FIG. 2) that enable the bone screw 10 to be more easily inserted into cancellous bone. Ideally, the varying depth follows the contour or taper of the screw body itself. The flute 28 is a tapering cut made essentially parallel to a longitudinal axis of the bone screw 10. The flute 28 preferably begins near or at the bone screw point 24, and extends toward the bone screw head 22 with decreasing depth of cut into the bone screw threads 26. Ideally, the varying depth follows the contour or taper of the screw body itself. The flute 28 can extend partially or completely to the bone screw head 22. Multiple fluting, as shown in FIG. 3 is a preferred embodiment of the invention. Multiple flutes may preferably be equally spaced in a radial fashion about the bone screw 10 for most efficient use. In operation, the edges of flute 28 cuts into the material, forming internal threads in the material that can engage with bone screw threads 26.

A further feature of the flute 28 is the placement of a cutting flute edge 29 in an alignment with the cannula 20. When multiple flutes are used, each flute would preferentially be aligned in a similar manner. This alignment has been found to increase the ease of insertion of the bone screw 10 in the proper position.

The use and method of implantation of the present invention is demonstrated in the following example made with reference to FIG. 5. Details of the procedure are available in the article *A Biomechanical Comparison of Different Surgical Techniques of Graft Fixation in Anterior Cruciate Ligament Reconstruction*. Kurosaka et al., Am. Jour, Sports Med. Vol. 15, No. 3 pp. 225-229, herein incorporated by reference. A knee joint 50 is a joint formed between a femur 34 and an inferior tibia 36 and fibula 38. The knee joint 50 is stabilized by a number of ligaments (not shown in FIG. 5 for the purpose of clarity) such as the patellar tendon, the quadriceps femoris tendon, lateral and medial collateral ligaments, and the anterior and posterior cruciate ligament. An anterior cruciate ligament 30, completely detached from its normal bony attachment point, is shown during reconstructive surgery illustrated in FIG. 5.

A necessary preliminary to the replacement of the anterior cruciate ligament 30 is the permanent attachment of the ligament substitute 30 to a femoral bone block 31 and a tibial bone block 32. Generally, an autogenous tissue is utilized as the ligament substitute. The patellar tendon is considered to be the tissue of choice because of its strength, durability, and elasticity. Also, in most instances, the required part of the patellar tendon can be harvested with bones at both ends which can form the bone blocks 31, 32. The femoral bone block 31 and the tibial bone block 32 may be shaped into a roughly rectangular box-like configuration.

The replacement of the anterior cruciate ligament 30 requires that a femoral bone borehole 40 be made through cancellous bone 33 of the femur 34 at the site of normal femoral attachment of the anterior cruciate ligament. The diameter of the femoral bone borehole 40 is slightly greater than the width of the femoral bone block 31 such that the femoral bone block 31 can be inserted into the borehole 40. A tibial bone borehole 41 is also made through the tibia 36 at the corresponding site of normal tibial attachment of the anterior cruciate ligament 30, and has a diameter permitting insertion of a tibial bone block 32. The ligament substitute 30, respectively attached at both ends to the femoral bone block 31 and the tibial bone block 32 is drawn through femoral bone borehole 40 and the tibial bone borehole 41 in the tibia by use of tibial sutures 43. The femoral sutures 42 and the tibial sutures 43 are then simultaneously drawn tight in opposing directions, bringing the ligament substitute 30 into the desired position and with the desired tightness.

When the femoral bone block 31 is sited in the proper position in the femoral bone borehole 40, the guide pin 12, with guide pin point 14 leading, is inserted into the femoral bone borehole 40. A small hammer, not shown in the figures, can be used to gently tap the guide pin head 16, forcing a temporary seated insertion of the guide pin 12 into the cancellous bone 33 of the femur 34, or a hemostat can be used to grasp the pin 12 for stability. The guide pin 12 is then used to guide the bone screw 10 into the proper position parallel to the femoral bone block 31 and interposed between the femoral bone block 31 and an inner wall of the femoral bore hole 40.

The bone screw 10, once in the proper position adjacently superior and parallel to the femoral bone block 31, is driven using a hex head driver 44 that fits engaging means 27. The driver 44 has a driver head 46 that has a driver head cannula 46 with a diameter at least equal to the diameter of guide pin 12. This permits placement of the driver 46 without interference from the guide pin 12.

During screwing engagement, each turn of the bone screw 10 cuts internal threads (not shown) into the femoral bone block 31 and the cancellous bone 33 of the femur 34. The internal threads are cut by the edges of a flute 28, and permit a reduced application of torque to the screwing insertion means 27 for successful screwing insertion of bone screw 10 as compared to a non-fluted bone screw. Proper guidance of the bone screw 10 into the femoral bone borehole 40 during screwing insertion is accomplished by the use of the guide pin 12.

When the bone screw 10 is completely inserted, a tight interference fit between the femoral bone block 31 and the cancellous bone 33 of the femur will be created to significantly secure the bone block 31 in the desired position allowing early mobilization and thus speeding the healing process and providing superior tensile and compressive, and superior effective stiffness strength compared to other ligament replacement procedures.

The procedure for screwing engagement is analogously duplicated for the attachment made to the tibia 36. At the completion of the procedure, the replacement of anterior cruciate ligament 30 is complete except for the normal healing and recovery time that is required to ensure regrowth and permanent attachment of bone blocks 31, 32 to the femur 34 and the tibia 36 and regrowth and revitalization of the ligament substitute 30.

The previous example is purely for illustrative purposes and is not meant to limit the particular type of soft tissue reconstruction or ligament replacement that is enabled by the use of the present invention. As those skilled in the art can appreciate, a variety of different surgical procedures can involve the use of a cannulated self-tapping bone screw having a guide pin to improve the ease with which a correct isertion of the bone screw can be made.

What is claimed is:

1. A bone screw and bone plug assembly for securing bone plugs into a bone comprising:
    a bone screw having an axial cannula with an internal diameter and an exterior screw threading;
    a bone plug;
    engaging means for driving insertion of the bone screw into the bone and bone plug;
    at least two fluted grooves cut into said screw threading, to permit self-tapping of said bone screw into both said bone and bone plug;
    a guide pin having a diameter smaller than the internal diameter of said axial cannula, thereby permitting guided insertion of the bone screw.

2. The apparatus of claim 1 wherein a surface of the bone screw is composed of an osteointegrative material.

3. The apparatus of claim 1 wherein the at least two fluted grooves cut into said screw threading are equally spaced around the bone screw.

4. The apparatus of claim 1 wherein the engaging means is a socket cavity formed in said bone screw.

5. A method for securing a bone plug element to a bone comprising the steps of:
    forming a bone borehole;
    inserting a bone plug into said borehole;
    situating a guide pin in the bone borehole adjacent to said plug;
    fitting a bone screw having a bone screw threading, an axial cannula with a diameter greater than said guide pin, and an at least two fluted grooves cut into the bone screw threading to enable self-tapping, onto the guide pin; and
    screwing the bone screw into both said bone and said bone plug.

6. A bone screw and bone plug assembly for securing bone plugs into bore in a bone;
    a bone plug;
    an elongated screw body formed to include an axial cannula and external screw threads;
    at least one fluted groove found in the screw threads at a position substantially adjacent one end of the screw body and parallel to a central longitudinal axis of the screw body; and
    a drive recess formed in the other end of the screw body for receiving a drive device to permit the bone screw to be simultaneously screwed into the bone and the bone plug.

7. The bone screw and bone plug assembly of claim 6, wherein the at least one fluted groove includes a radially inner edge and a radially outer edge and wherein the radially inner edge is generally parallel to and in alignment with a plane extending through the center of the axial cannula.

8. The bone screw and bone plug assembly of claim 7, wherein there are four fluted grooves formed in the screw threads, with the four grooves equally spaced around the circumference of the screw body.

9. The bone screw and bone plug assembly of claim 7, wherein the at least one fluted groove extends from the position substantially adjacent the one end of the screw body a specified distance toward the other end of the screw body, and wherein the depth of the fluted groove decreases in the direction from the first end toward the second end.

10. A bone screw and bone plug assembly for securing bone plugs into a bone comprising:
    a bone screw having an axial cannula with an internal diameter and an exterior screw threading;
    a bone plug;
    engaging means for driving insertion of the bone screw into the bone and bone plug;
    said bone screw exterior screw threading being able to be screwed into both said bone and bone plug to securely position the bone plug with respect to the bone through an interference fit with the bone screw;
    a guide pin having a diameter smaller than the internal diameter of said axial cannula, thereby permitting guided insertion of the bone screw.

11. The apparatus of claim 10 wherein a surface of the bone screw is composed of an osteointegrative material.

12. The apparatus of claim 10 wherein the engaging means is a socket cavity formed in said bone screw.

13. A method for securing a bone plug element to a bone comprising the steps of:
    forming a bone borehole;
    inserting a bone plug into said borehole;
    situating a guide pin in the bone borehole adjacent to said plug;
    fitting a bone screw having a bone screw threading and an axial cannula with a diameter greater than said guide pin, onto the guide pin; and
    screwing the bone screw into both said bone and said bone plug to securely position the bone plug with respect to the bone through an interference fit with the bone screw.

14. A bone screw and bone plug assembly for securing bone plugs into bore in a bone;
    a bone plug;
    an elongated screw body formed to include an axial cannula and external screw threads at a position substantially adjacent one end of the screw body and parallel to a central longitudinal axis of the screw body; and a drive recess formed in the other end of the screw body for receiving a drive device to permit the bone screw to be simultaneously screwed into the bone and the bone plug to securely position the bone plug with respect to the bone through an interference fit with the bone screw.

* * * * *

UNITED STATES PATENT AND TRADEMARK OFFICE
CERTIFICATE OF CORRECTION

PATENT NO.   :   4,950,270
DATED        :   August 21, 1990
INVENTOR(S)  :   Bowman et al.

It is certified that error appears in the above-identified patent and that said Letters Patent is hereby corrected as shown below:

On the bibliography page, at [75], the second named inventor's name "Richard V. Zile" should be changed to --Richard Van Zile--.

On the bibliography page, under "OTHER PUBLICATIONS", "John B. McGirrty" should be changed to --John B. McGinty--.

Signed and Sealed this

Twenty-first Day of January, 1992

Attest:

HARRY F. MANBECK, JR.

*Attesting Officer*   *Commissioner of Patents and Trademarks*